(12) United States Patent
Faerber (10) Patent No.: US 12,036,076 B2
(45) Date of Patent: Jul. 16, 2024

(54) LAMINAR AIR FLOW DEVICE AND SYSTEM

(71) Applicant: Thomas H. Faerber, Overland Park, KS (US)

(72) Inventor: Thomas H. Faerber, Overland Park, KS (US)

(73) Assignee: Thomas H. Faerber, Overland Park, KS (US)

( * ) Notice: Subject to any disclaimer, the term of this patent is extended or adjusted under 35 U.S.C. 154(b) by 748 days.

(21) Appl. No.: 17/223,566

(22) Filed: Apr. 6, 2021

(65) Prior Publication Data

US 2021/0307873 A1 Oct. 7, 2021

Related U.S. Application Data

(60) Provisional application No. 63/127,287, filed on Dec. 18, 2020, provisional application No. 63/104,032, filed on Oct. 22, 2020, provisional application No. 63/061,488, filed on Aug. 5, 2020, provisional application No. 63/039,821, filed on Jun. 16, 2020, provisional application No. 63/013,083, filed on Apr. 21, 2020, provisional application No. 63/009,684, filed on Apr. 14, 2020, provisional application No. 63/005,701, filed on Apr. 6, 2020.

(51) Int. Cl.
| | |
|---|---|
| *A61B 90/40* | (2016.01) |
| *A61B 46/20* | (2016.01) |
| *A61B 50/33* | (2016.01) |
| *A61B 90/50* | (2016.01) |

(52) U.S. Cl.
CPC ............. *A61B 90/40* (2016.02); *A61B 46/20* (2016.02); *A61B 50/33* (2016.02); *A61B 90/50* (2016.02); *A61B 2046/201* (2016.02); *A61B 2090/401* (2016.02); *A61B 2217/005* (2013.01)

(58) Field of Classification Search
CPC ......... A61B 90/40; A61B 90/50; A61B 46/20; A61B 2046/201; A61B 2090/401; A61B 2217/005
USPC ...................................... 454/56, 63
See application file for complete search history.

(56) References Cited

U.S. PATENT DOCUMENTS

| | | | | |
|---|---|---|---|---|
| 3,635,522 A | * | 1/1972 | Kerwit | A61G 15/10 297/118 |
| 3,859,993 A | * | 1/1975 | Bitner | A61M 16/009 5/507.1 |

(Continued)

FOREIGN PATENT DOCUMENTS

WO 2016160840 10/2016

*Primary Examiner* — Avinash A Savani
*Assistant Examiner* — Dana K Tighe
(74) *Attorney, Agent, or Firm* — Hovey Williams LLP (57) ABSTRACT

A medical instrument tray for supporting medical instruments and connecting to a medical vacuum hose and evacuating gases and debris from a procedure area to reduce spread of airborne bacteria, viruses, or other contaminates comprises an upper surface and a laminar air flow suction device. The upper surface supports the medical instruments. The laminar air flow suction device extends below the upper surface and comprises a first opening and a second opening. The first opening is configured to connect to the medical vacuum hose and has a first opening width. The second opening has a second opening width that is wider than the first opening width.

6 Claims, 8 Drawing Sheets

(56) References Cited

U.S. PATENT DOCUMENTS

| | | | | |
|---|---|---|---|---|
| 4,275,719 | A | * | 6/1981 | Mayer .................... A61B 90/40 128/849 |
| 4,281,986 | A | | 8/1981 | Erickson |
| 4,446,861 | A | | 5/1984 | Tada |
| 4,802,851 | A | | 2/1989 | Rhoades |
| 4,936,318 | A | * | 6/1990 | Schoolman .......... A61G 13/108 15/301 |
| 5,015,243 | A | * | 5/1991 | Schifano ............... B08B 15/007 604/315 |
| 5,127,411 | A | | 7/1992 | Schoolman et al. |
| 5,140,997 | A | * | 8/1992 | Glassman .............. A61B 46/00 128/857 |
| 5,730,153 | A | * | 3/1998 | Chang .................... A61B 46/00 128/857 |
| 6,302,109 | B1 | * | 10/2001 | Parnes ................... A61B 46/00 128/845 |
| 6,464,499 | B1 | | 10/2002 | Lu |
| 6,663,610 | B1 | * | 12/2003 | Thompson .............. A61M 1/84 604/128 |
| 8,568,391 | B2 | | 10/2013 | Kerns et al. |
| 8,708,985 | B2 | * | 4/2014 | Schultz .................. A61M 1/84 604/319 |
| 9,310,088 | B2 | | 4/2016 | Melikov et al. |
| 10,398,452 | B2 | | 9/2019 | Palmerton et al. |
| 10,702,435 | B2 | * | 7/2020 | Kirschman ................ A61L 9/18 |
| 2020/0281686 | A1 | * | 9/2020 | Finkelstein ............ A61B 46/20 |
| 2020/0345350 | A1 | * | 11/2020 | Gorek ............. A61B 17/06161 |

* cited by examiner

LAMINAR AIR FLOW DEVICE AND SYSTEM

RELATED APPLICATIONS

This non-provisional patent application claims priority to U.S. Provisional Patent Application Ser. No. 63/127,287 filed on Dec. 18, 2020, and entitled "PACD SYSTEM AEROSOL EVACUATION GLOVES AND EVACUATION TUBE ACCESSORY APPLICATIONS"; U.S. Provisional Patent Application Ser. No. 63/104,032 filed on Oct. 22, 2020, and entitled "PATIENT ATMOSPHERE CONTROL DEVICE (PACD) SYSTEM"; U.S. Provisional Patent Application Ser. No. 63/061,488 filed on Aug. 5, 2020, and entitled "PACD SYSTEM—EVACUATION TUBING/TRAY ADDENDUM"; U.S. Provisional Patent Application Ser. No. 63/039,821 filed on Jun. 16, 2020, and entitled "PACD HAND PIECE EVACUATION TUBING"; U.S. Provisional Patent Application Ser. No. 63/013,083 filed on Apr. 21, 2020, and entitled "PATIENT ATMOSPHERE CONTROL DEVICE: PACD"; U.S. Provisional Patent Application Ser. No. 63/009,684 filed on Apr. 14, 2020, and entitled "PATIENT ATMOSPHERE CONTROL DEVICE: PACD"; and U.S. Provisional Patent Application Ser. No. 63/005,701 filed on Apr. 6, 2020, and entitled "PATIENT ATMOSPHERE CONTROL DEVICE: PACD". The disclosures of these applications are incorporated by reference herein in their entireties.

BACKGROUND

Room air purification devices turn room air over at certain cycles per hour, but these devices do not remove aerosols, vapors, smoke, or other atmosphere contaminants directly adjacent to a patient or a procedure area. Aerosols and some vapors disperse with a high velocity and reach speeds that exceed the capabilities of air purification devices. Aerosol dissemination has been found to extend over 10 feet from a patient during a procedure. With the recent COVID-19 pandemic and previous events such as the outbreaks of Zika, Ebola, SARS, MERS, etc., patients and healthcare providers face persistent environmental infectious threats. Additionally, there is potential for an increase in worldwide tuberculosis cases due to a worldwide quarantine, variant strains of COVID-19 will likely be present for several years, and threats will remain for other infectious entities.

The background discussion is intended to provide information related to the present invention which is not necessarily prior art.

SUMMARY

The present invention solves the above-described problems and other problems by providing a medical instrument tray and medical evacuation system for more effectively evacuating gases and debris from a procedure area to reduce spread of airborne bacteria, viruses, or other contaminates.

A medical instrument tray constructed in accordance with an embodiment of the present invention is operable to support medical instruments and connect to a medical vacuum hose. The medical instrument tray comprises an upper surface and a laminar air flow suction device. The upper surface supports the medical instruments.

The laminar air flow suction device extends below the upper surface and comprises a first opening and a second opening. The first opening is configured to connect to the medical vacuum hose and has a first opening width. The second opening has a second opening width that is wider than the first opening width. By supporting instruments on the upper surface, the laminar air flow suction device can be in closer proximity to the procedure area, which reduces the amount of gases and debris leaving the area. Further, the second opening width being wider than the first causes a laminar flow of air so that the laminar air flow suction device better captures the gases and debris from the procedure area.

Another embodiment of the invention is a medical evacuation system for evacuating gases and debris from a procedure area. The medical evacuation system includes a vacuum source, a flexible hose, and a laminar air flow suction device. The vacuum source includes a connection port, and the flexible hose is connected to the connection port. The laminar air flow suction device is in fluid communication with the flexible hose and includes a first opening and a second opening. The first opening is coupled to the hose and has a first opening width. The second opening has a second opening width that is wider than the first opening width. The laminar air flow suction device connected to the flexible hose allows the suction device to be positioned in various equipment, such as a pocket of a surgical drape.

A medical evacuation system for evacuating gases and debris from a procedure area according to another embodiment of the invention includes a vacuum source, a hose, an articulating support arm, an instrument tray, and a laminar air flow suction device. The vacuum source includes a connection port, and the hose is connected to the connection port. The articulating support arm supports the hose. The instrument tray is supported on a distal end of the support arm and includes a bottom surface.

The laminar air flow suction device extends from the bottom surface of the instrument tray and includes a first opening and a second opening. The first opening is connected to the hose and has a first opening width. The second opening has a second opening width that is wider than the first opening width. By supporting the laminar air flow suction device and the instrument tray on the articulating support arm, the instruments on the tray can be proximate to the procedure area, and the suction device can better evacuate gases and debris from the procedure area.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
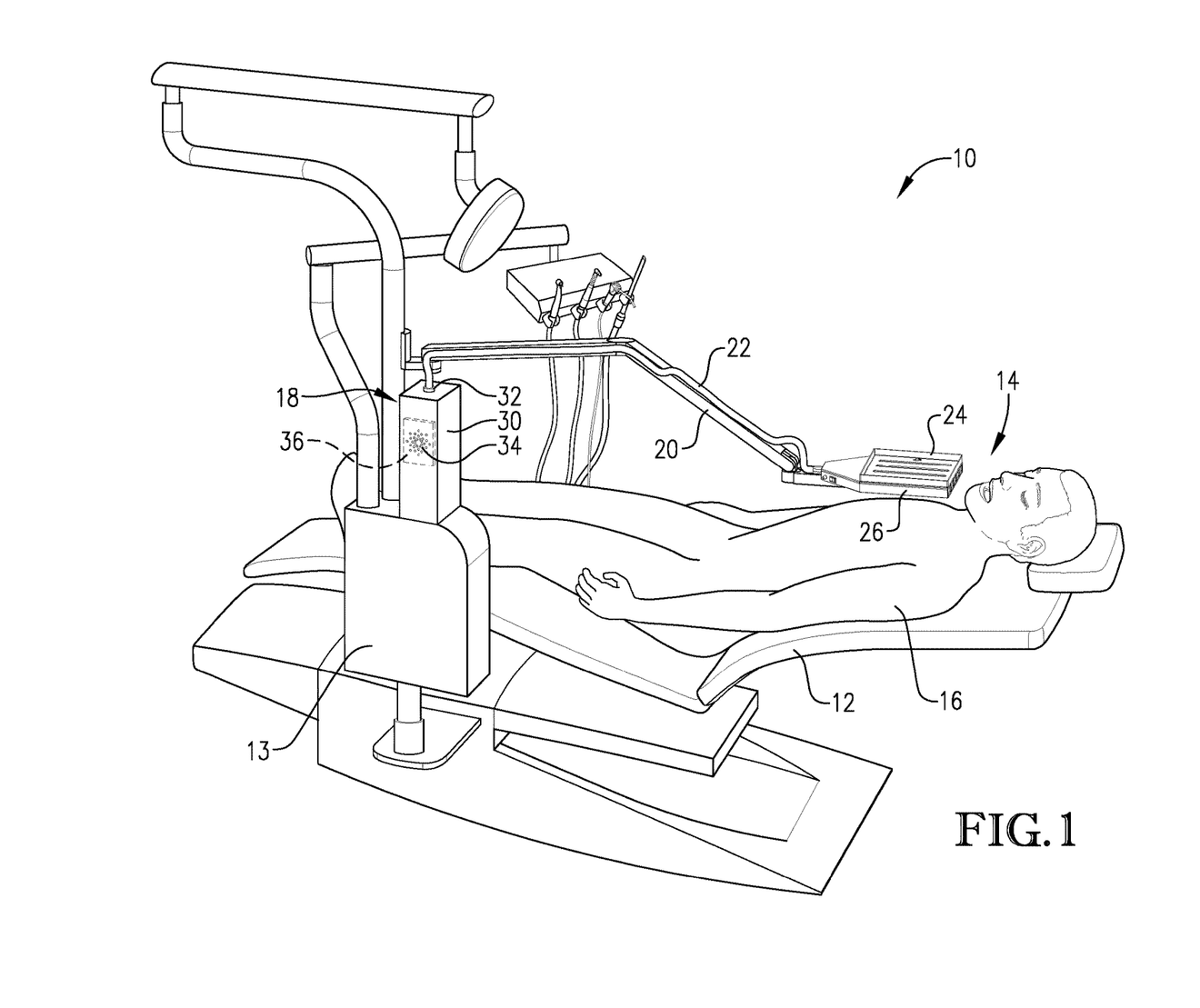
FIG. 1 is a perspective view of a medical evacuation system constructed in accordance with an embodiment of the present invention shown in use with a patient.

A medical evacuation system 10 constructed in accordance with an embodiment of the invention is illustrated in FIG. 1. The evacuation system 10 is positioned next to a medical chair 12 generally used for oral procedures or examinations, such as dental, orthodontic, periodontic, etc. The evacuation system 10 may also be used for other types of procedures or examinations, including maxillofacial procedures, plastic surgery, orthopedic surgery, ENT surgery, etc. While the evacuation system 10 is depicted positioned adjacent a medical chair 12 generally used for dental applications, the evacuation system 10 may be positioned next to or integrated with any type of medical chair 12 for any type of procedure or examination without departing from the scope of the present invention.

Figure 2:
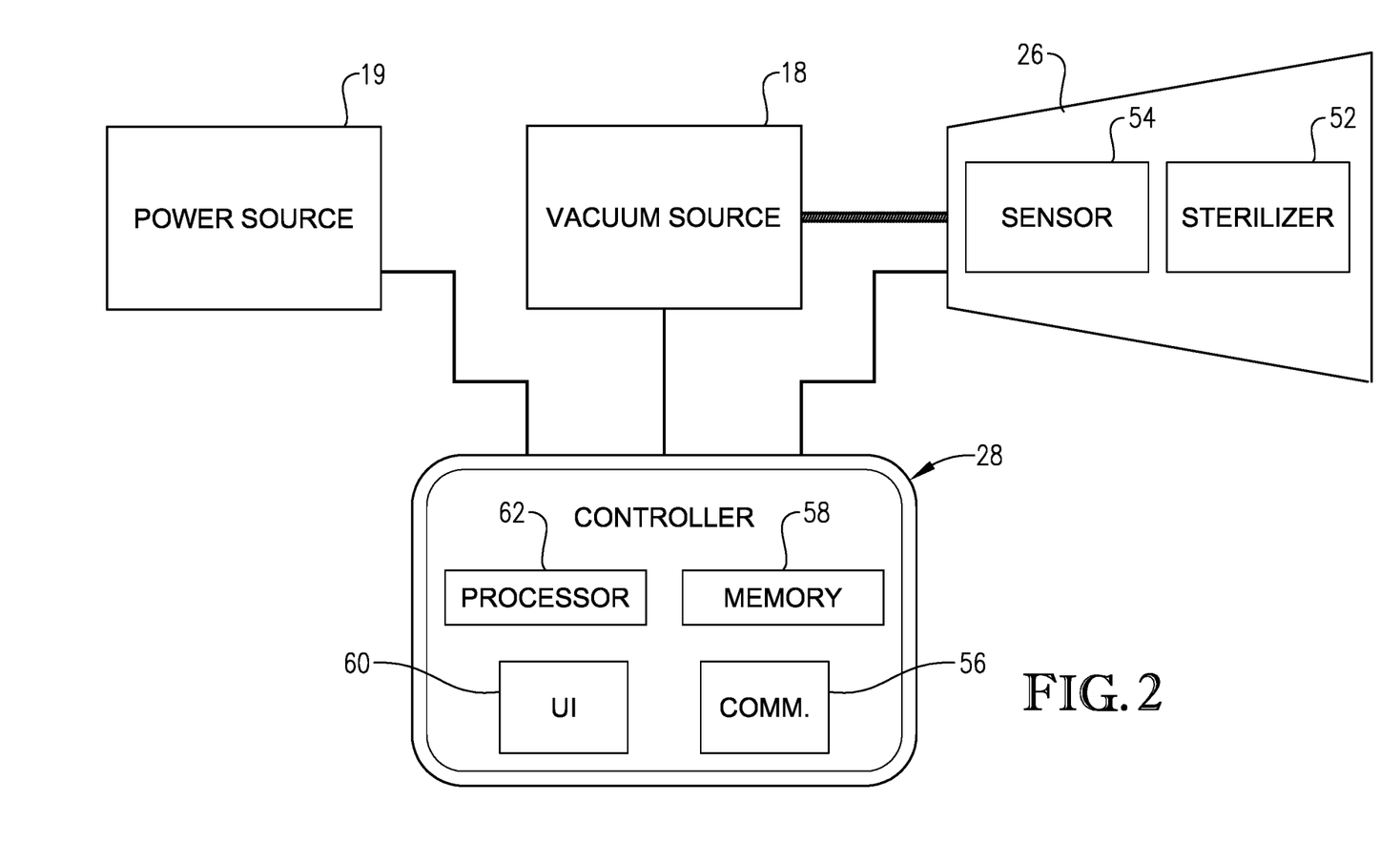
FIG. 2 is a schematic diagram depicting selected components of the medical evacuation system of FIG. 1.

The evacuation system 10 is operable to evacuate debris, gases, smoke, and aerosols from a procedure area 14 proximate to a patient 16. The evacuation system 10 comprises a vacuum source 18, an articulating support arm 20, a flexible hose 22, an instrument tray 24, a laminar air flow suction device 26, and a controller 28 (depicted in FIG. 2). The vacuum source 18 provides negative pressure to enable the suction device 26 to pull air form the procedure area 14. The vacuum source 18 may be positioned on a stand 13 adjacent to the chair 12 and may comprise a housing 30 having a port 32 and an outlet 34, one or more motors (not shown) for moving air through the housing 30, and one or more filter 36. The port 32 is operable to couple to the flexible hose 22 and allows air to enter the housing 30 therethrough. The outlet 34 is operable to allow air to exit the housing 30 into the procedure room and/or through another hose (not shown) that directs the air elsewhere, such as outside the procedure room or outdoors. The filter 36 is configured to filter air traveling through the vacuum source 18 and may comprise a HEPA filter, an ULPA filter, a membrane filter, a nano-fiber filter, a carbon filter, a gas filter, a catalyst filter, an antimicrobial filter, a charcoal filter, or the like. The vacuum source 18 is depicted as being positioned on the stand 13 next to the chair 12; however, the vacuum source 18 may be located elsewhere without departing from the scope of the present invention. For example, the vacuum source 18 may be remote and located away from the procedure area 14, and its port 32 located near the procedure area 14 connected by a network of tubes, ducts, or the like. In some embodiments, the vacuum source 18 may be powered by a power source 19, such as a generator, battery, or the like (as schematically depicted in FIG. 2).

The articulating arm 20 may be anchored on the vacuum source 18 and/or the stand 13 and is configured to pivot, bend, or otherwise change orientation to position the suction device 26 near the procedure area 14 over the patient 16. The articulating arm 20 may support the hose 22 and include one or more hinges, joints, or the like. The flexible hose 22 is in fluid communication with the port 32 of the vacuum source 18 and directs air from the suction device 26 to the vacuum source 18.

Figure 3:
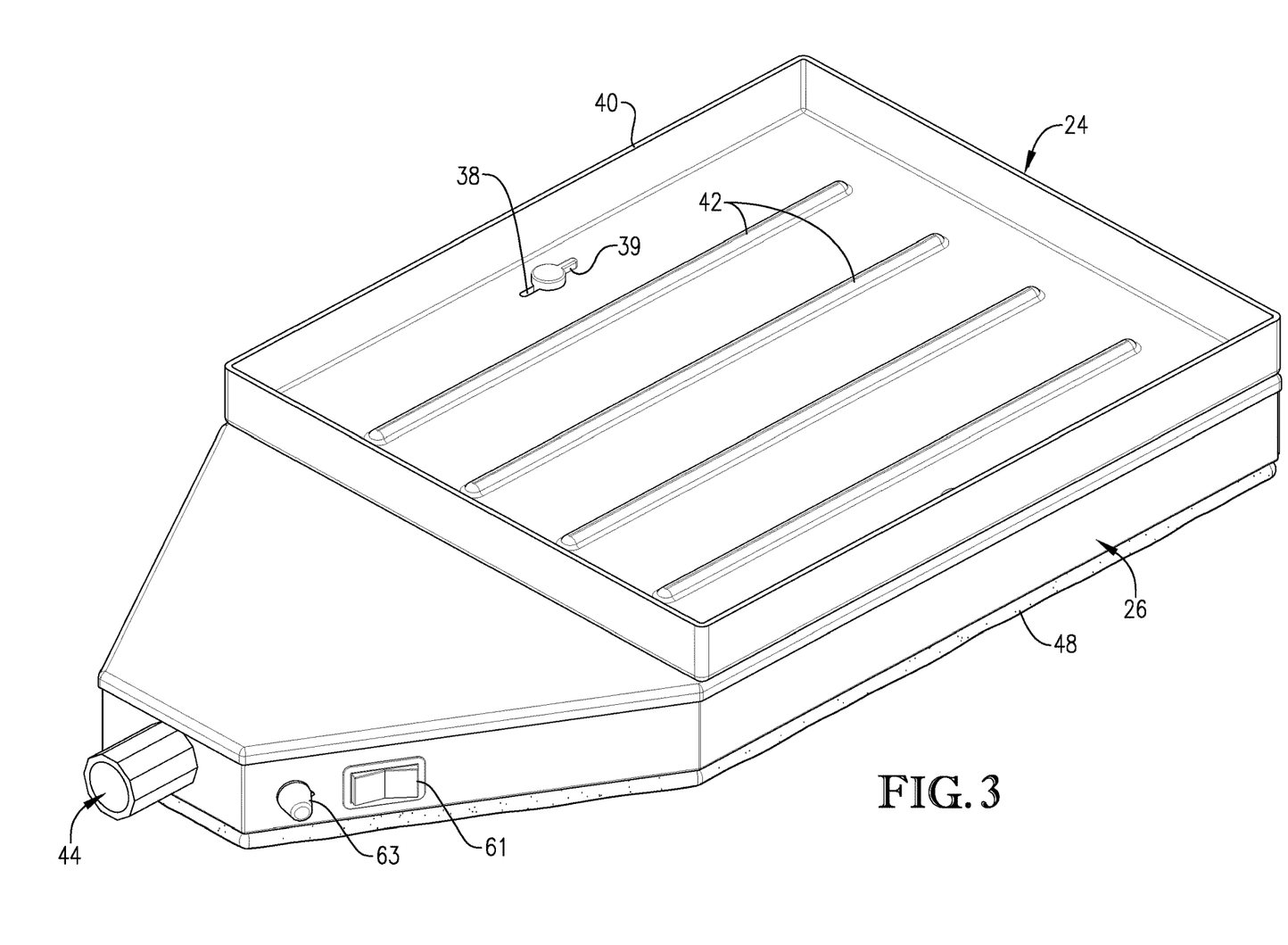
FIG. 3 is a top view of a laminar air flow suction device of the medical evacuation system of FIG. 1 with an instrument tray attached.
Figure 4:
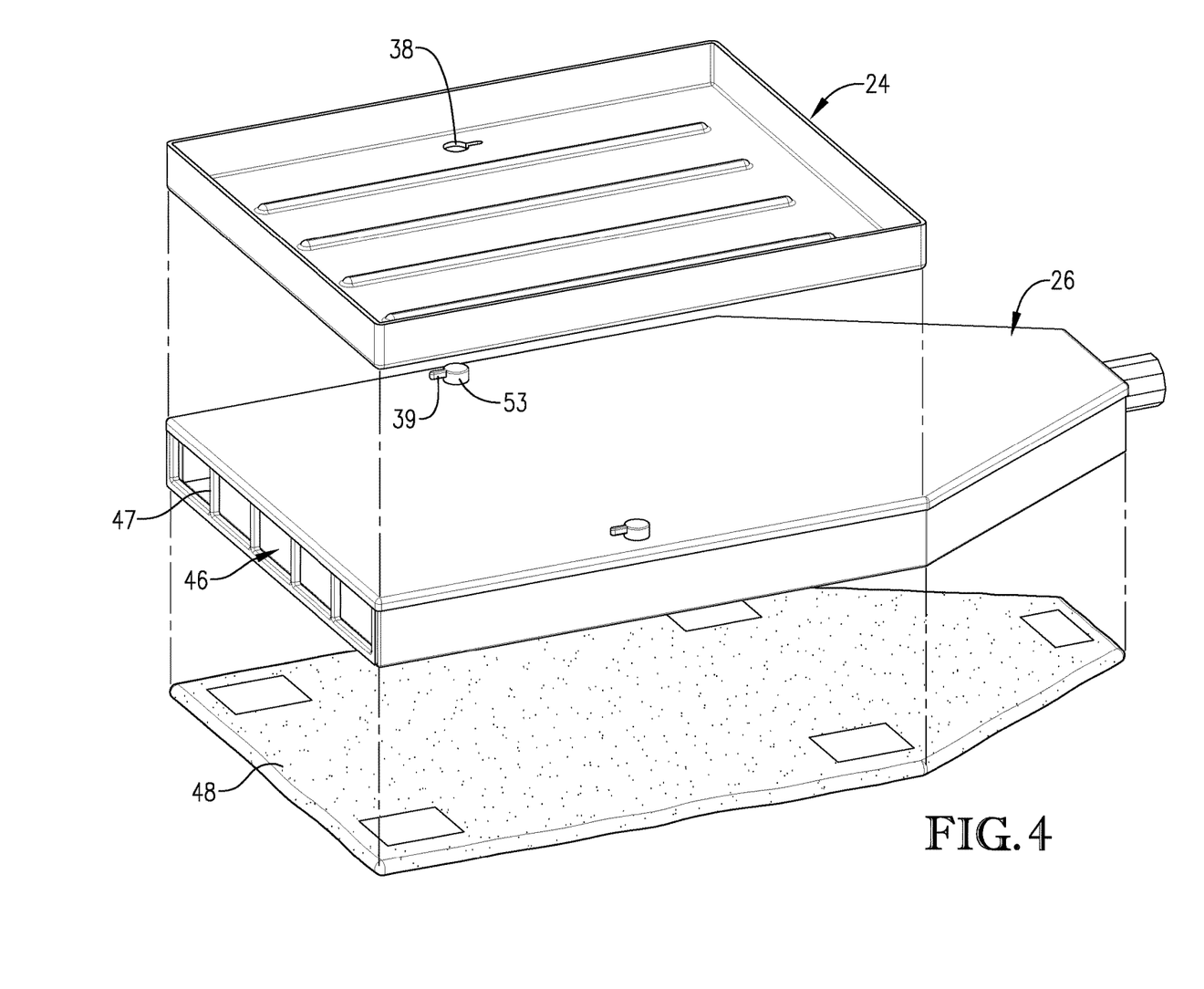
FIG. 4 is an exploded view of select components of the medical evacuation system of FIG. 1.
Figure 5:
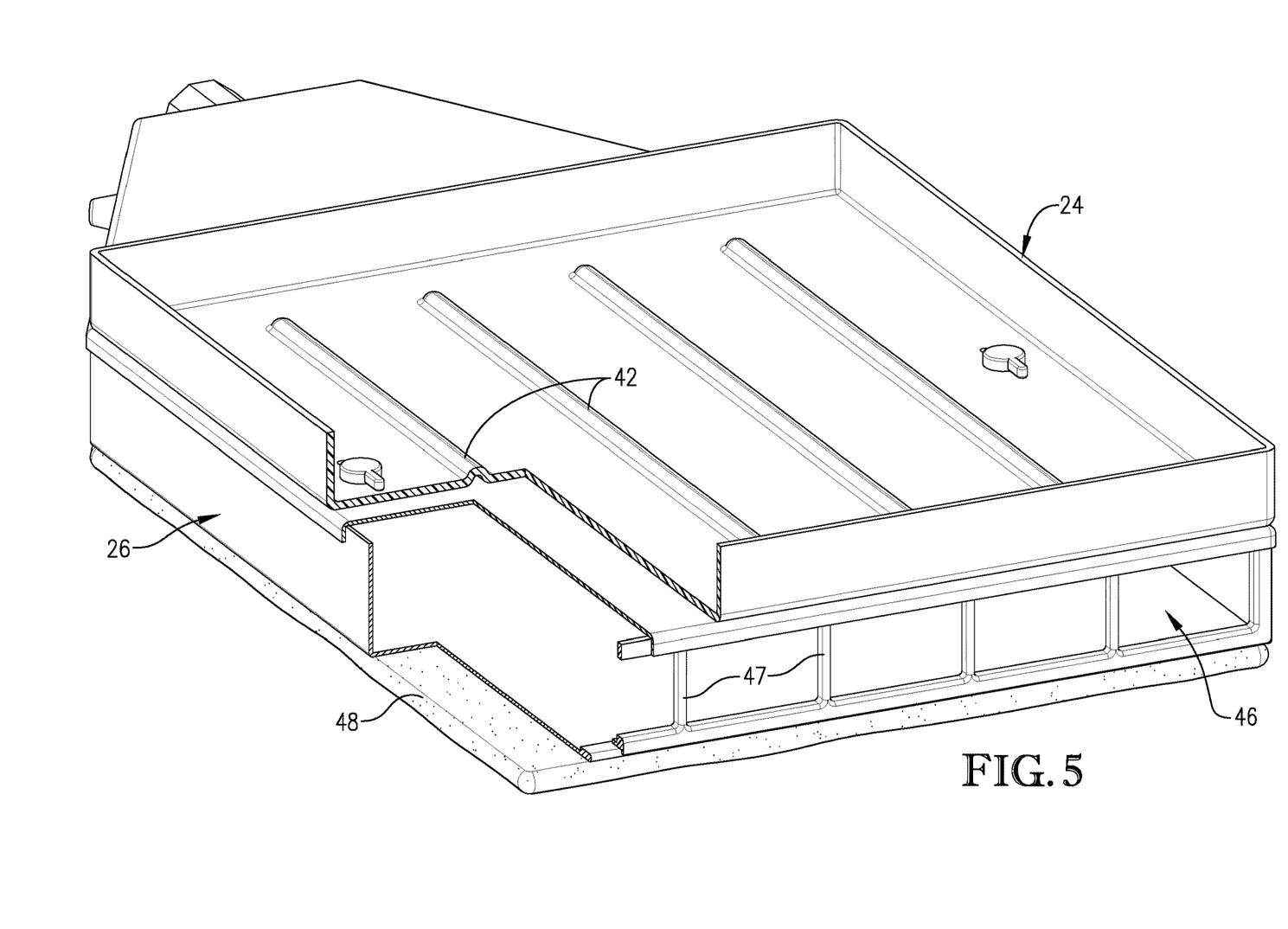
FIG. 5 is a sectional perspective view of select components of the medical evacuation system of FIG. 1.

Turning to FIGS. 3-5, the instrument tray 24 provides a surface to place instruments used during the examination or procedure and is supported by the articulating arm 20. The instrument tray 24 may be positioned above the suction device 26. In some embodiments, the instrument tray 24 and the suction device 26 are integrated into one piece. The instrument tray 24 may include one or more attachment mechanisms 38 for attaching to the suction device 26. In some embodiments, the attachment mechanisms 38 comprise magnets that couple to the suction device 26 and/or magnets of the suction device 26. The tray 24 may include one or more walls 40 for holding instruments on the upper surface of the tray 24 and one or more ridges 42 for organizing the instruments.

The suction device 26 is operable to receive gas, debris, smoke, and/or aerosols pulled from the procedure area 14. The suction device 26 includes a first opening 44 for coupling to the hose 22 and a second opening 46 for positioning near the procedure area 14. The first opening 44 may have a width or area that is significantly smaller than the width or area of the second opening 46. For example, the ratio of the area of the second opening 46 to the area of the first opening 44 may be 10:1, 50:1, or 100:1. In some embodiments, the first opening 44 and the second opening 46 may have the about the same heights, but the second opening 46 width may be much wider than the first opening 44 width. The second opening 46 is generally much wider than it is tall which produces laminar air flow from the procedure area 14. In some embodiments, the second opening 46 may have a height of about 6 mm to about 38.1 mm and a width of about 50 mm to about 320 mm. In some embodiments, the second opening 46 may have a height of 17 mm to about 22 mm and a width of about 135 mm to about 235 mm. The ratio of the width of the second opening 46 to its height may be about 5:1, 10:1, 8:1, and in preferred embodiments 8.4:1. The suction device 26 may have a length so that the first opening 44 and the second opening 46 are spaced apart by a distance about 200 mm to about 520 mm. In some embodiments, the suction device 26 may include a bottom surface 48 that is contoured for resting on the torso of the patient 16. In some embodiments, the bottom surface 48 may comprise padding. In some embodiments, the suction device 26 may also include attachment mechanisms 39 complementary to the attachment mechanisms 38 of the instrument tray 24. The attachment mechanisms 39 may comprise magnets 53 for coupling the instrument tray 24 to the top surface of the suction device 26. The magnets 53 may also be positioned to couple instruments to the tray 24. In some embodiments, the hose 22, tray 24, and suction device 26 comprise materials capable of withstanding heated gases, embers from burning procedures, etc., such as metals, high density rubber, polytetrafluoroethylene (PTFE), or the like. In some embodiments, the system 10 may include flame retardant material positioned in the hose 22, tray 24, and suction device 26.

In some embodiments, the suction device 26 includes a sterilizing device 52 and one or more sensor 54 positioned in the suction device 26 (as depicted in FIG. 2). The sterilizing device 52 may be configured to sterilize air flowing into the suction device 26 from the procedure area 14. The sterilizing device 52 may comprise an ultraviolet (UV) light source providing UV light purification, an ozone generator, and/or an ionizer configured to emit charged ions. In embodiments that include the ionizer, the sterilizing device 52 may include one or more points of ionization, accompanying grounding plate(s), and a deposition surface. The deposition surface may comprise charges opposite to the charged ions, such as an electric filter and uncharged material adapted to capture particles charged by the charged ions. The controller 28 may be configured to control ion generation rate of the ionizer 52 and vacuum power of the vacuum source 18 with adjustable flow rates and adjustable power requirements. The sensor 54 may be configured to detect levels of harmful aerosols and industrial vapors to send a control signal for airflow adjustments as well as power adjustments, rate of ionizer production, or a deposition surface charge density of a deposition surface. In some embodiments, the suction device 26 may include one or more guards 47 positioned at the second opening 46 configured to prevent objects such gauze pads, small instrument components, and the like from being sucked into the device 26.

Turning back to FIG. 2, the controller 28 may comprise a communication element 56, a memory element 58, a user interface 60, and a processing element 62. The communication element 56 may generally allow communication with systems or devices external to the system 10, such as a smart phone, tablet, and/or a laptop/desktop computer. The communication element 56 may include signal or data transmitting and receiving circuits, such as antennas, amplifiers, filters, mixers, oscillators, digital signal processors (DSPs), and the like. The communication element 56 may establish communication wirelessly by utilizing RF signals and/or data that comply with communication standards such as cellular 2G, 3G, 4G, 5G, or LTE, WiFi, WiMAX, Bluetooth®, BLE, or combinations thereof. The communication element 56 may be in communication with the processing element 62 and the memory element 58. The communication element 56 may receive signals representative of commands from a user to activate the vacuum source 18, increase power of the vacuum source 18, activate the sterilizing device 52, or increase the power output of the sterilizing device 52.

The memory element 58 may include data storage components, such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 58 may be embedded in, or packaged in the same package as, the processing element 62. The memory element 58 may include, or may constitute, a "computer-readable medium". The memory element 58 may store the instructions, code, code segments, software, firmware, programs, applications, apps, services, daemons, or the like that are executed by the processing element 62.

The user interface 60 generally allows the user to utilize inputs and outputs to interact with the controller 28 and is in communication with the processing element 62. Inputs may include buttons, pushbuttons, knobs, jog dials, shuttle dials, directional pads, multidirectional buttons, switches, keypads, keyboards, mice, joysticks, microphones, or the like, or combinations thereof. The outputs of the user interface 60 may include a display but may include any number of additional outputs, such as audio speakers, lights, dials, meters, printers, or the like, or combinations thereof, without departing from the scope of the present invention. In some embodiments, a portion of the user interface 60 may be positioned on the instrument tray 24, which enables a user to readily adjust the controls of the vacuum source 18. For example, the user interface 60 may include a switch 61 and dial 63 positioned on the suction device 26 for easy control by the user.

The processing element 62 may include processors, microprocessors (single-core and multi-core), microcontrollers, DSPs, field-programmable gate arrays (FPGAs), analog and/or digital application-specific integrated circuits (ASICs), or the like, or combinations thereof. The processing element 62 may generally execute, process, or run instructions, code, code segments, software, firmware, programs, applications, apps, processes, services, daemons, or the like. The processing element 62 may also include hardware components such as finite-state machines, sequential and combinational logic, and other electronic circuits that can perform the functions necessary for the operation of the current invention. The processing element 62 may be in communication with the other electronic components through serial or parallel links that include address busses, data busses, control lines, and the like.

For example, the processing element 62 may be configured to control ion generation rate of the ionizer 52 and vacuum power of the vacuum source 18 with adjustable flow rates with adjustable power requirements. The processing element 62 may be configured to control these parameters based on signals received from the sensors 54 representative of levels of harmful aerosols and industrial vapors.

An exemplary method of using the medical evacuation system 10 will now be described. The suction device 26 may be positioned on the torso of the patient 16. The instrument tray 24 may then be coupled to the suction device 26 via the attachment mechanisms 38, 39. Instruments used for the procedure may be placed on the instrument tray 24. The vacuum source 18 may be turned on via the switch 61, dial 63, the user interface 60, and/or a signal from an external device received via the communication device 56. The vacuum source 18 may pull air from the procedure area 14 into the suction device 26, through the hose 22, into the housing 30, through the filter 36, and out through the outlet 34. The sterilizing device 52 may also be turned on in this manner. The sensors 54 may be configured to detect characteristics of the air being pulled into the suction device 26 and send signals representative of the characteristics to the processing element 62. The processing element 62 may be configured to adjust one or more operating parameters of the vacuum source 18 and/or the sterilizing device 52 based on the characteristics of the air pulled into the suction device 26.

Figure 6:
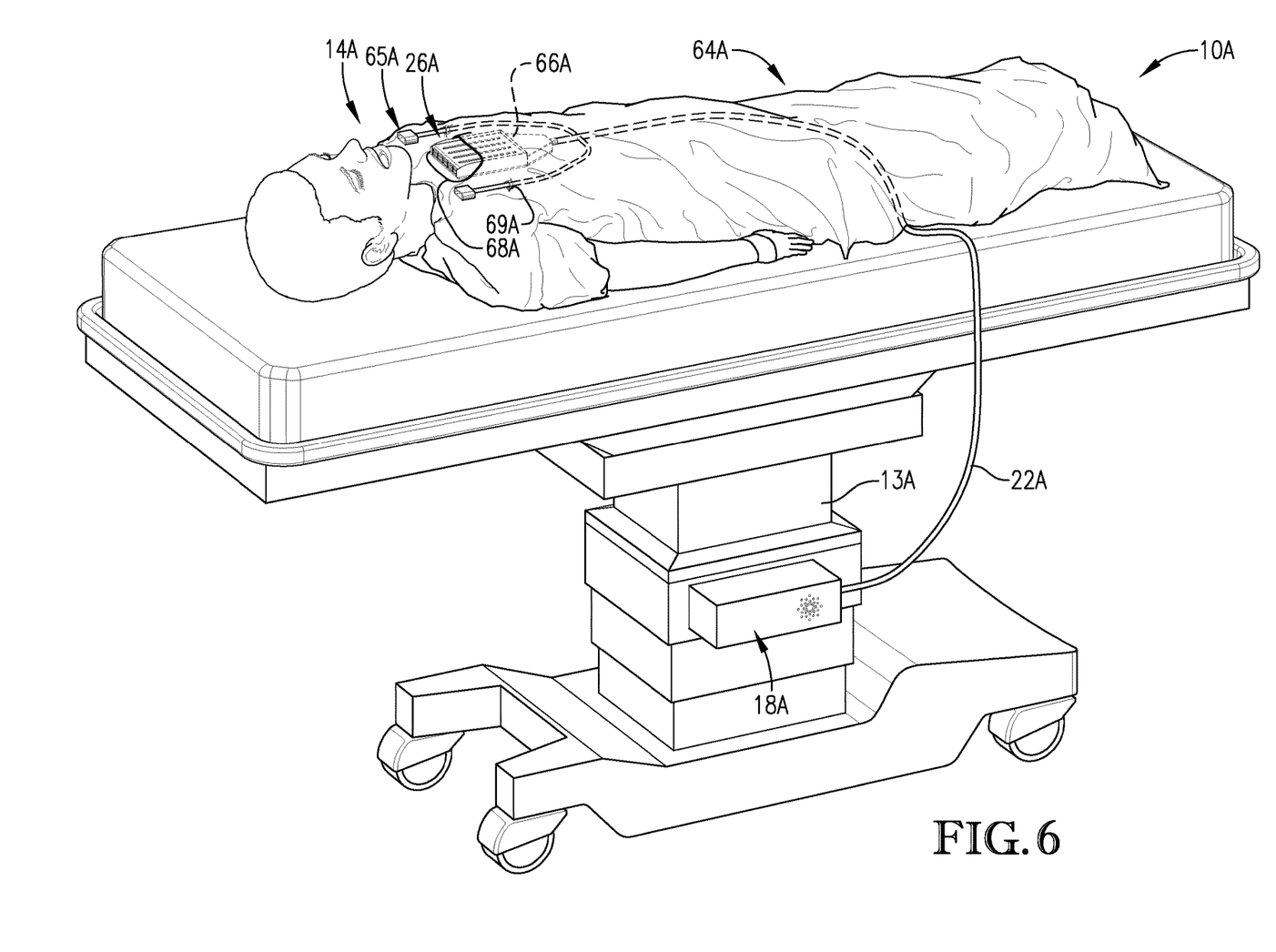
FIG. 6 is a perspective view of a medical evacuation system according to another embodiment of the present invention.
Figure 7:
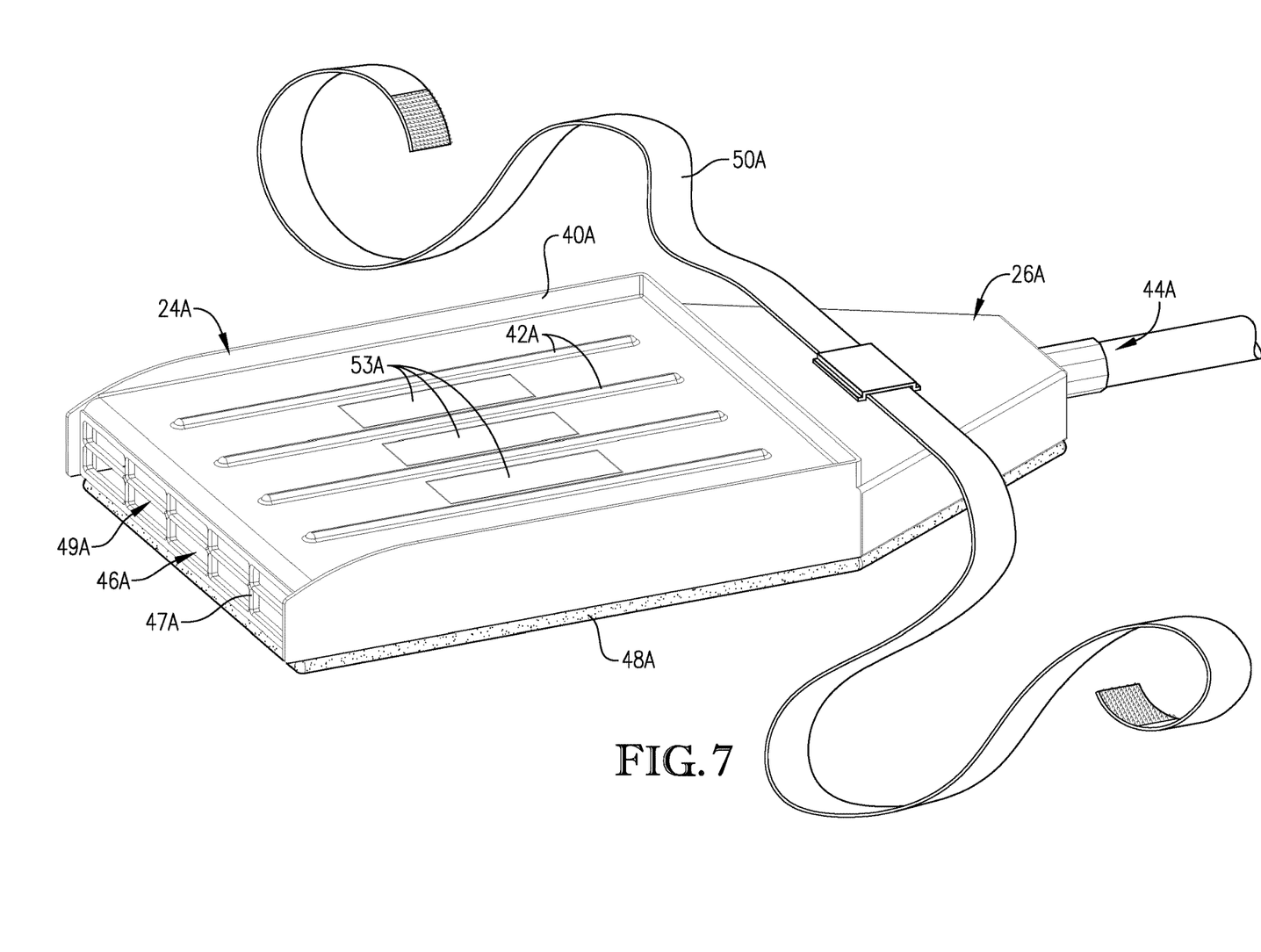
FIG. 7 is a perspective view a laminar air flow suction device of the medical evacuation system of FIG. 6.
Figure 8:
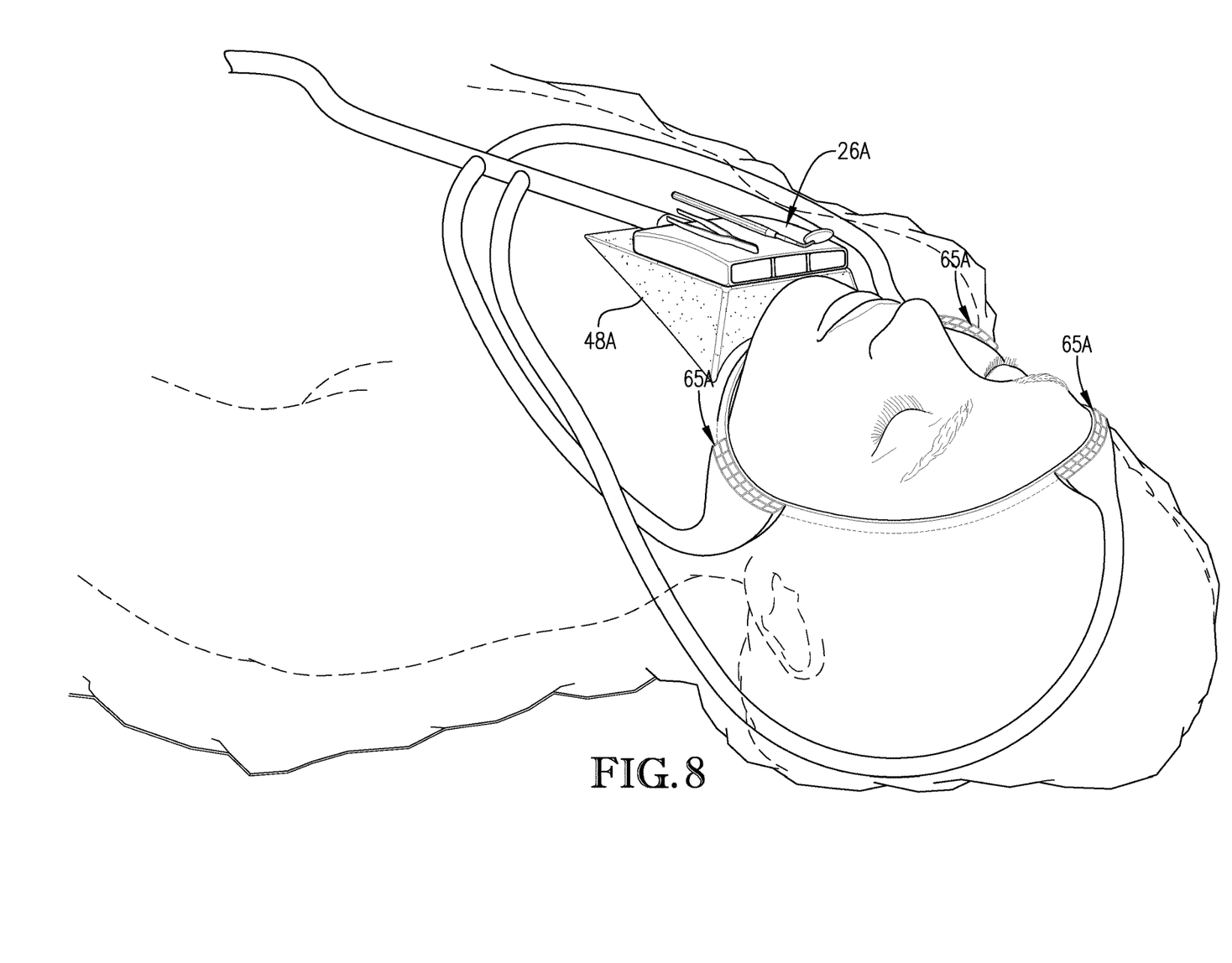
FIG. 8 is a perspective view of the medical evacuation system of FIG. 6 with instruments secured on the laminar air flow suction device.

A medical evacuation system 10A constructed in accordance with another embodiment of the invention is shown in FIGS. 6-8. The medical evacuation system 10A may comprise substantially similar components as medical evacuation system 10; thus, the components of medical evacuation system 10A that correspond to similar components in medical evacuation system 10 have an 'A' appended to their reference numerals.

The medical evacuation system 10A includes all the features of the medical evacuation system 10, except the articulating arm 20, and further comprises a surgical drape 64A and a pair of smaller suction devices 65A. The surgical drape 64A includes a pocket 66A for receiving the laminar air flow suction device 26A and securing the suction device 26A near the procedure area 14A. The drape 64A may also include one or more openings 69A for allowing the smaller suction devices 65A to extend therethrough. The pocket 66A includes an opening 68A which allows air around the procedure area 14A to enter the suction device 26A. The drape 64A may comprise washable material, recyclable material, and/or disposable material, such as plastic or the like. While the suction devices 26A, 65A are depicted as being positioned below the patient's mouth, the suction devices 26A, 65A may be positioned anywhere about the procedure area 14A without departing from the scope of the present invention. For example, one or more of the suction devices 26A, 65A may be draped over the patient's forehead.

Further, the laminar air flow suction device 26A of the medical evacuation system 10A is significantly smaller than the laminar air flow suction device 26. The suction device 26A may have a height less than 3.5 millimeters. In some embodiments, the second opening 46A may have a height of about 2 mm to about 3 mm and a width of about 10 mm to about 50 mm. The ratio of the width of the second opening 46A to its height may be about 5:1, 10:1, 8:1, and in preferred embodiments 8.4:1. The suction device 26A may have a length so that the first opening 44A and the second opening 46A are spaced apart by a distance about 50 mm to about 100 mm. The suction device 26A comprises an upper surface that functions as the instrument tray 24A, which may include one or more magnets 53A for securing instruments to the upper surface 24A (as depicted in FIG. 8). The suction device 26A may also include straps 50A for securing the device 26A to the patient 16A. The guard 47A may further include a crossbar 49A for preventing gauze pads or other items from getting pulled into the suction device 26A. In some embodiments, the air flow suction device 26A may be secured to the hand and/or wrist of a doctor, dentist, surgeon, etc. The device 26A may be secured over the gloves of the hand and/or wrist. This allows the device 26A to be in very close proximity to the procedure/examination area 14A and pull air directly away from the area 14A.

Additional Considerations

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the current technology can include a variety of combinations and/or integrations of the embodiments described herein.

Although the present application sets forth a detailed description of numerous different embodiments, it should be understood that the legal scope of the description is defined by the words of the claims set forth in any subsequent regular utility patent application. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as computer hardware that operates to perform certain operations as described herein.

In various embodiments, computer hardware, such as a processing element, may be implemented as special purpose or as general purpose. For example, the processing element may comprise dedicated circuitry or logic that is permanently configured, such as an application-specific integrated circuit (ASIC), or indefinitely configured, such as an FPGA, to perform certain operations. The processing element may also comprise programmable logic or circuitry (e.g., as encompassed within a general-purpose processor or other programmable processor) that is temporarily configured by software to perform certain operations. It will be appreciated that the decision to implement the processing element as special purpose, in dedicated and permanently configured circuitry, or as general purpose (e.g., configured by software) may be driven by cost and time considerations.

Accordingly, the term "processing element" or equivalents should be understood to encompass a tangible entity, be that an entity that is physically constructed, permanently configured (e.g., hardwired), or temporarily configured (e.g., programmed) to operate in a certain manner or to perform certain operations described herein. Considering embodiments in which the processing element is temporarily configured (e.g., programmed), each of the processing elements need not be configured or instantiated at any one instance in time. For example, where the processing element comprises a general-purpose processor configured using software, the general-purpose processor may be configured as respective different processing elements at different times. Software may accordingly configure the processing element to constitute a particular hardware configuration at one instance of time and to constitute a different hardware configuration at a different instance of time.

Computer hardware components, such as communication elements, memory elements, processing elements, and the like, may provide information to, and receive information from, other computer hardware components. Accordingly, the described computer hardware components may be regarded as being communicatively coupled. Where multiple of such computer hardware components exist contemporaneously, communications may be achieved through signal transmission (e.g., over appropriate circuits and buses) that connect the computer hardware components. In embodiments in which multiple computer hardware components are configured or instantiated at different times, communications between such computer hardware components may be achieved, for example, through the storage and retrieval of information in memory structures to which the multiple computer hardware components have access. For example, one computer hardware component may perform an operation and store the output of that operation in a memory device to which it is communicatively coupled. A further computer hardware component may then, at a later time, access the memory device to retrieve and process the stored output. Computer hardware components may also initiate communications with input or output devices, and may operate on a resource (e.g., a collection of information).

The various operations of example methods described herein may be performed, at least partially, by one or more processing elements that are temporarily configured (e.g., by software) or permanently configured to perform the relevant operations. Whether temporarily or permanently configured, such processing elements may constitute processing element-implemented modules that operate to perform one or more operations or functions. The modules referred to herein may, in some example embodiments, comprise processing element-implemented modules.

Similarly, the methods or routines described herein may be at least partially processing element-implemented. For example, at least some of the operations of a method may be performed by one or more processing elements or processing element-implemented hardware modules. The performance of certain of the operations may be distributed among the one or more processing elements, not only residing within a single machine, but deployed across a number of machines. In some example embodiments, the processing elements may be located in a single location (e.g., within a home environment, an office environment or as a server farm), while in other embodiments the processing elements may be distributed across a number of locations.

Unless specifically stated otherwise, discussions herein using words such as "processing," "computing," "calculating," "determining," "presenting," "displaying," or the like may refer to actions or processes of a machine (e.g., a computer with a processing element and other computer hardware components) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

The patent claims at the end of this patent application are not intended to be construed under 35 U.S.C. § 112(f) unless traditional means-plus-function language is expressly recited, such as "means for" or "step for" language being explicitly recited in the claim (s).

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A medical evacuation system for evacuating gases and debris from a procedure area to reduce spread of airborne bacteria, viruses, or other contaminates, the medical evacuation system comprising:
   a vacuum source with a connection port;
   a hose connected to the connection port;
   an articulating support arm supporting the hose;
   an instrument tray supported at a distal end of the articulating support arm and including a bottom surface, a top surface, and a plurality of magnets operable to secure instruments to the top surface of the instrument tray; and
   a laminar air flow suction device extending from the bottom surface of the instrument tray and comprising—
      a first opening connected to the hose and having a first opening width and a first opening height that is less than the first opening width,
      a second opening having a second opening width that is at least five times wider than the first opening width and a second opening height that is less than the second opening width, and
      a guard configured to extend over a portion of the second opening.

2. The medical evacuation system of claim 1, wherein the laminar air flow suction device comprises a bottom surface with a deformable padding material.

3. The medical evacuation system of claim 1, wherein the first opening height and the second opening height are substantially equal.

4. The medical evacuation system of claim 1, wherein the laminar air flow suction device includes one or more magnets, and the instrument tray comprises a metallic tray coupled to the laminar air flow suction device via the one or more magnets.

5. The medical evacuation system of claim 1, wherein the vacuum source comprises a housing having an air outlet and a filter positioned so that air exiting the housing through the air outlet is filtered via the filter.

6. The medical evacuation system of claim 5, wherein the filter comprises at least one of a HEPA filter, an ULPA filter, a membrane filter, a nano-fiber filter, a carbon filter, a gas filter, a catalyst filter, an anti-microbial filter, or a charcoal filter.

\* \* \* \* \*